US010365216B2

(12) United States Patent
Zhang et al.

(10) Patent No.: US 10,365,216 B2
(45) Date of Patent: Jul. 30, 2019

(54) ADVANCED IN-SITU PARTICLE DETECTION SYSTEM FOR SEMICONDUCTOR SUBSTRATE PROCESSING SYSTEMS

(71) Applicant: Applied Materials, Inc., Santa Clara, CA (US)

(72) Inventors: Lin Zhang, San Jose, CA (US); Xuesong Lu, Santa Clara, CA (US); Andrew V. Le, San Jose, CA (US); Fa Ji, Dublin, CA (US); Jang Seok Oh, San Ramon, CA (US); Patrick L. Smith, Vancouver, WA (US); Shawyon Jafari, Sunnyvale, CA (US); Ralph Peter Antonio, Los Gatos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/793,458

(22) Filed: Oct. 25, 2017

(65) Prior Publication Data

US 2018/0156727 A1 Jun. 7, 2018

Related U.S. Application Data

(60) Provisional application No. 62/429,508, filed on Dec. 2, 2016.

(51) Int. Cl.
*G01N 21/53* (2006.01)
*G01N 1/22* (2006.01)
(Continued)

(52) U.S. Cl.
CPC ............... *G01N 21/53* (2013.01); *G01N 1/22* (2013.01); *H01L 21/67017* (2013.01);
(Continued)

(58) Field of Classification Search
CPC ... G01N 15/0205; G01N 21/53; G01N 1/2247
See application file for complete search history.

(56) References Cited

U.S. PATENT DOCUMENTS 5,416,594 A * 5/1995 Gross ................. G01B 11/0633
356/237.5
6,707,545 B1 3/2004 Hunter
(Continued)

FOREIGN PATENT DOCUMENTS

KR 10-2010-0037784 4/2010
KR 10-1565091 B1 11/2015

OTHER PUBLICATIONS

International Search Report and Written Opinion dated Feb. 13, 2018 for Application No. PCT/US2017/058352.
(Continued)

*Primary Examiner* — Tri T Ton
(74) *Attorney, Agent, or Firm* — Patterson + Sheridan, LLP

(57) ABSTRACT

An FI having an in-situ particle detector and a method for particle detection therein are provided. In one aspect, the FI includes a fan, a substrate support, a particle detector, and an exhaust outlet. The fan, substrate support, and particle detector are arranged such that, in operation, the fan directs air towards the exhaust outlet and over a substrate on the substrate support to create laminar flow. The particle detector, positioned downstream from the substrate support and upstream from the exhaust outlet, analyzes the air and detects particle concentration before the particles are exhausted. The collected particle detection data may be combined with data from other sensors in the FI and used to identify the source of particle contamination. The particle detector may also be incorporated into other system com-
(Continued)

ponents, including but not limited to, a load-lock or buffer chamber to detect particle concentration therein.

19 Claims, 5 Drawing Sheets

(51) Int. Cl.
    *H01L 21/67*     (2006.01)
    *H01L 21/677*     (2006.01)
    *G01N 15/02*     (2006.01)
    *G01N 15/00*     (2006.01)
    *G01N 15/06*     (2006.01)

(52) U.S. Cl.
    CPC .. *H01L 21/67253* (2013.01); *H01L 21/67778* (2013.01); *G01N 1/2247* (2013.01); *G01N 15/0205* (2013.01); *G01N 2015/0046* (2013.01); *G01N 2015/0693* (2013.01)

(56) References Cited

U.S. PATENT DOCUMENTS

| | | | |
|---|---|---|---|
| 6,779,226 | B2 | 8/2004 | Hunter et al. |
| 7,012,684 | B1 | 3/2006 | Hunter |
| 2006/0045669 | A1 | 3/2006 | Namioka et al. |
| 2006/0225299 | A1 | 10/2006 | Kim et al. |
| 2009/0317214 | A1* | 12/2009 | Hsiao ................ H01L 21/67017 414/217 |
| 2015/0116710 | A1* | 4/2015 | Nicoletti ............ G01N 15/1484 356/338 |

OTHER PUBLICATIONS

Taiwan Office Action dated Mar. 12, 2019 for Application No. 106138016.

\* cited by examiner

US 10,365,216 B2

ADVANCED IN-SITU PARTICLE DETECTION SYSTEM FOR SEMICONDUCTOR SUBSTRATE PROCESSING SYSTEMS

CROSS-REFERENCE TO RELATED APPLICATIONS

This application claims benefit of U.S. Provisional Patent Application Ser. No. 62/429,508, filed on Dec. 2, 2016, which is herein incorporated by reference in its entirety.

BACKGROUND

Field

Aspects disclosed herein relate to systems and methods for semiconductor manufacturing, and more specifically to systems and methods for in-situ particle detection.

Description of the Related Art

In semiconductor manufacturing, a clean, contamination-free processing environment contributes to maximizing overall process yield. This is particularly true as substrate circuitry and geometries shrink to a nanometer (nm) scale since particles become more likely to cause defects and yield loss. Particle detection in each of the processing environments within the processing system, including the factory interface (FI), helps reduce or eliminate particle contaminants in the system. Conventional particle detection methods for the FI include use of a handheld particle detection device.

One problem with the use of a handheld particle detection device is that detection only occurs when the FI is open, for example, at initial installation or during preventative maintenance. Additionally, since the particle detection readings are infrequent, identifying the source of the particle contamination and troubleshooting the problem takes a great amount of time, during which the system is down and other sensors in the FI may not be operating.

Therefore, there is a need for improved systems and methods for particle monitoring in an FI.

SUMMARY

An FI having an in-situ particle detector and a method for particle detection therein are provided. In one aspect, the FI includes a fan, a substrate support, a particle detector, and an exhaust outlet. The fan, substrate support, and particle detector are arranged such that, in operation, the fan directs air towards the exhaust outlet and over a substrate on the substrate support to create laminar flow. The particle detector, positioned downstream from the substrate support and upstream from the exhaust outlet, analyzes the air and detects particle concentration before the particles are exhausted. The collected particle detection data may be combined with data from other sensors in the FI and used to identify the source of particle contamination for more efficient troubleshooting. The particle detector may also be incorporated into other system components, including but not limited to, a load-lock or buffer chamber to detect particle concentration therein.

In one aspect, a factory interface is disclosed. The factory interface includes a fan, a substrate support positioned downstream from the fan, a particle detector coupled to an inner surface of the factory interface and positioned downstream from the substrate support, a particle detector tube coupled to the particle detector and open to a location within the factory interface, and an exhaust outlet positioned downstream from the particle detector.

In another aspect, a particle detection system is disclosed. The particle system includes a particle detector positioned downstream from a fan and a substrate support in a factory interface, a server connected to the particle detector, the server being connected to one or more additional sensors positioned in the factory interface and being configured to collect particle concentration data from the particle detector and the one or more additional sensors in the factory interface, and a network coupled to the server, the network being configured to communicate particle concentration data to one or more equipment operators.

In yet another aspect, a method for in-situ particle detection in a semiconductor manufacturing system is disclosed. The method includes receiving a substrate in a factory interface through a factory interface door, transferring the substrate from the factory interface to a transfer chamber or a process chamber through a load-lock slit door, transferring the substrate from the transfer chamber or the process chamber to a substrate support in the factory interface through the load-lock slit door, and continuously monitoring particle concentration in the factory interface during the transferring the substrate from the factory interface to the transfer chamber or the process chamber through the load-lock slit door and from the transfer chamber or the process chamber to the substrate support in the factory interface through the load-lock slit door.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of scope, as the disclosure may admit to other equally effective aspects.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

An FI having an in-situ particle detector and a method for particle detection therein are provided. In one aspect, the FI includes a fan, a substrate support, a particle detector, and an exhaust outlet. The fan, substrate support, and particle detector are arranged such that, in operation, the fan directs air towards the exhaust outlet and over a substrate on the substrate support to create laminar flow. The particle detector, positioned downstream from the substrate support and upstream from the exhaust outlet, analyzes the air and detects particle concentration before the particles are exhausted. The collected particle detection data may be combined with data from other sensors in the FI and used to identify the source of particle contamination for more efficient troubleshooting. The particle detector may also be incorporated into other system components, including but not limited to, a load-lock or buffer chamber to detect particle concentration therein.

Figure 1:
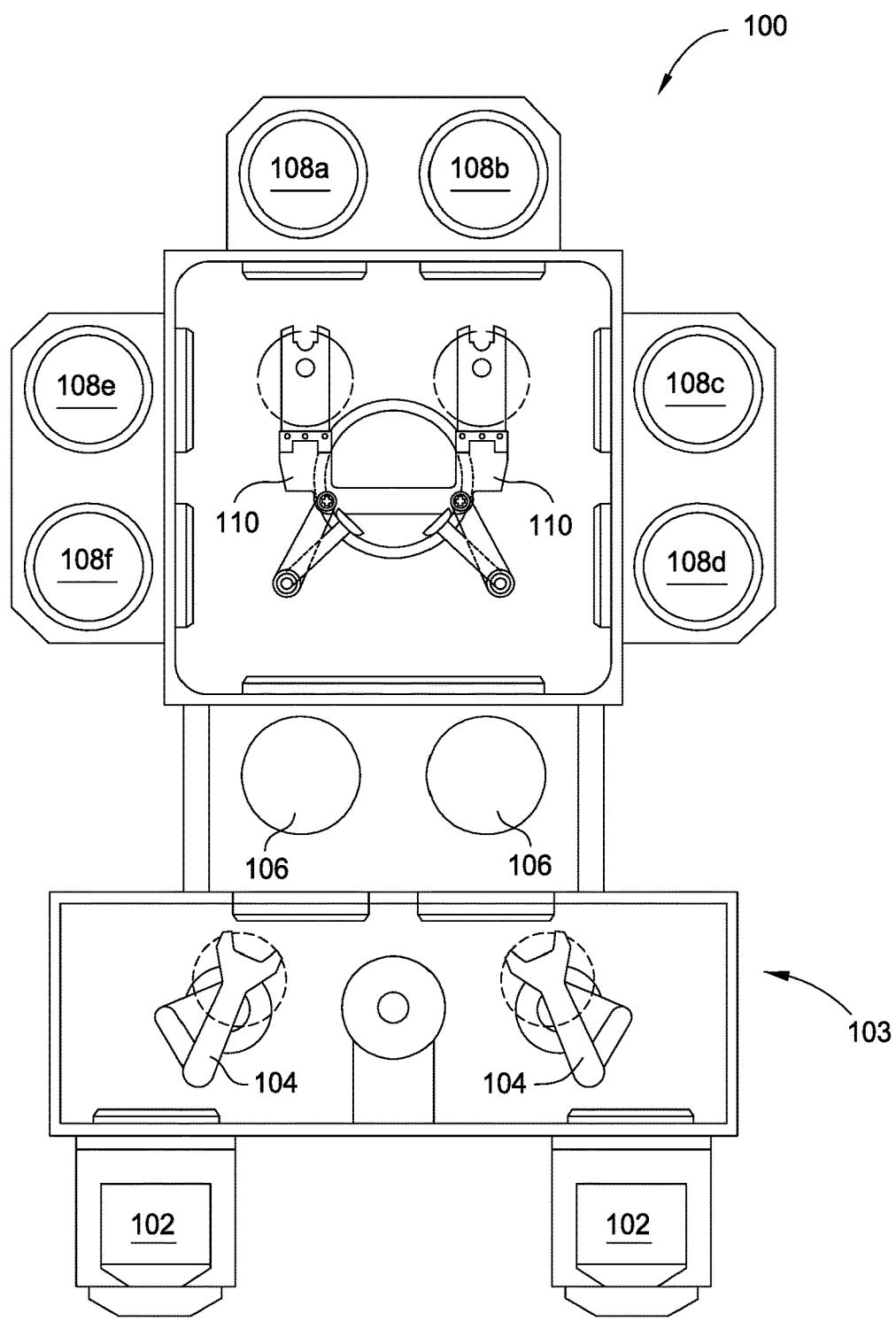
FIG. 1 is a substrate processing system, according to an aspect of the disclosure.

FIG. 1 is a substrate processing system 100 according to an aspect of the disclosure. As shown in FIG. 1, a pair of front opening unified pods (FOUPs) 102 supplies substrates that are received by robotic arms 104 from a factory interface 103 and placed into a low-pressure holding area 106 before being placed into one of the substrate processing chambers 108a-108f. A second robotic arm 110 may be used to transport the substrates from the low-pressure holding area 106 to the substrate processing chambers 108a-108f and back. Substrate processing chambers 108a-108f may include one or more system components for depositing, annealing, curing and/or etching a film formed on the substrate.

Figure 2:
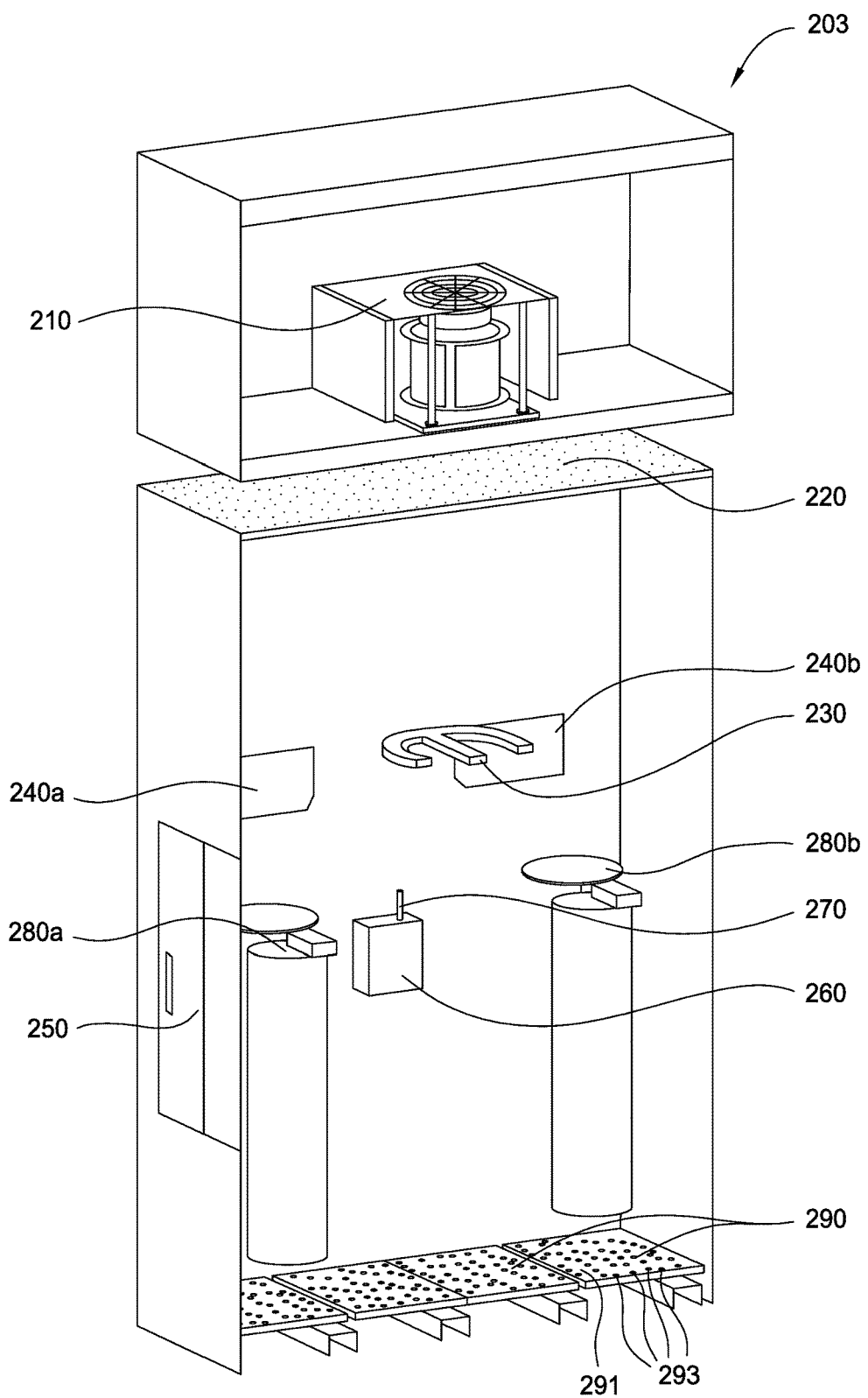
FIG. 2 is a cross-sectional view of an FI having in-situ particle detection capabilities, according to an aspect of the disclosure.

FIG. 2 is a cross-sectional view of an FI 203 having in-situ particle detection capabilities. The FI 203 may be used in place of the FI 103 in FIG. 1. The FI 203 includes a fan 210, a filter 220, a substrate support 230, load-lock slit doors 240a, 240b, an FI door 250, a particle detector 260, a particle detector tube 270, a first substrate holder and effector robot 280a, a second substrate holder and effector robot 280b, and an exhaust outlet 290. The FI 203 optionally further includes sensors, including but not limited to, fan speed sensors and/or pressure sensors (not shown). Each of the aforementioned components is generally coupled to one or more walls of the FI 203 by any suitable coupling means. For example, the particle detector 260 can be coupled to one or more walls of the FI 203 by a bracket manufactured to couple the particle detector 260 to the particular FI. The FI 203 may also include further components, such as a cooling station below the substrate support 230.

In the aspect of FIG. 2, the fan 210, substrate support 230, and particle detector 260 are arranged in a vertical configuration. More specifically, the fan 210 is disposed in an upper portion of the FI 203 and is configured to direct air downward through an opening positioned beneath the fan 210 (not shown), through the filter 220 to a lower portion of the FI 203, the substrate support 230 is positioned below the fan 210, and the particle detector 260 is positioned below the substrate support 230. The substrate support 230 includes a multi-bladed support structure having openings therebetween to facilitate airflow vertically within the FI. The particle detector 260 may be positioned any suitable distance below the substrate support 230, such as several inches below the substrate support 230, for example between about 1 and about 24 inches, such as between about 5 and about 15 inches. The substrate support 230 is also positioned proximate to and between the first substrate holder and effector robot 280a and the second substrate holder and effector robot 280b. While FIG. 2 shows a vertical configuration, other configurations in which the substrate support 230 is positioned downstream from the fan 210 and the particle detector 260 is positioned downstream from the substrate support 230, such as a horizontal configuration, are also contemplated herein. Other configurations include arrangements in which the relative locations of the fan 210, the substrate support 230, the particle detector 260, and the exhaust outlet 290 provide suitable results.

The filter 220 acts as a first barrier to prevent particle contamination in the FI 203. The filter 220 is generally any suitable filter, for example, a porous plate of plastic material having pores sized to restrict downward directed flow of particles into the FI 203. The filter 220 facilities removal of particles from air or other gases directed downward by the fan 210.

The particle detector 260 is a remote detector for detecting particles as small as about 50 nm up to particles as large as about 25 micrometers (μm). One example of a particle detector 260 is a scattered laser detector. The particle detector 260 generally includes a pump for drawing air from the environment within the FI 203 into the particle detector 260, a sensor for analyzing the sample air, a laser, and a detector of scattered laser. The particle detector 260 further includes at least one particle detector tube 270 for introducing air into the particle detector 260. FIG. 2 shows a single particle detector tube 270; however, the particle detector 260 generally includes any suitable number of particle detector tubes 270 disposed in any suitable configuration. In the example shown in FIG. 2, the particle detector tube extends upward from an upper surface of the particle detector 260 towards the fan 210. The laser and the detector are positioned downstream of the particle detector tube 270. Generally, when air passes through the laser beam produced by the laser, the particles cause laser scattering. The particle detector 260 analyzes the scattered laser emissions to identify particle concentration. In further examples, the particle detector 260 includes a multichannel system, for example six channels, with each channel being configured to detect particles within a particular size range. Some of the particle size ranges of each of the channels may overlap with the other channels. While the aspect of FIG. 2 includes one particle detector 260, other aspects may include multiple detectors located throughout the factory interface. Additionally, it is contemplated that the particle detector 260 is generally any suitable particle detector.

As described above, the particle detector tube 270 of FIG. 2, as an example, is a straight tube of any length. In one aspect, the tube lacks bending in order to align with the direction of the air stream through the FI 203 and to increase detection sensitivity. The particle detector tube 270 may include an opening at the top of the tube, i.e. the end distal to the particle detector 260, and/or an opening along the length of the tube directed toward some location within the FI 203. In one aspect, the opening is directed towards one of the load-lock slit doors 240a, 240b to monitor particles coming from the area of the load-lock slit door 240a or 240b. In another aspect, the opening is below the substrate support 230 to monitor particles coming from the top of the FI 203, such as particles that pass through the filter 220. In yet another aspect, the opening is directed towards the FI door 250 to monitor particles coming from the FI door 250. While one particle detector tube 270 is shown, the particle detector 260 may include a plurality of particle detector tubes 270 that are positioned within and open to or otherwise directed towards different locations within the FI 203.

As discussed above in the example of FIG. 2, the particle detector tube 270, or plurality of particle detector tubes 270, are generally substantially straight between the end connected to the particle detector 260 and the opening at the position for particle detection. However, in order to open to different locations within the FI 203, the plurality of particle detector tubes can include various bends and turns in order to reach the respective location; however, the opening will remain at a position configured to align with the direction of the movement of air through the FI 203. The different locations within the FI 203 for detection are generally selected to be those locations which can be used to most effectively capture the overall particle contamination and movement within the FI 203 based on process and hardware considerations.

In the example shown in FIG. 2, the exhaust outlet 290 includes a baffle plate 291 having a plurality of holes 293 through which particles are directed through a gas outlet and out of the Fl 203. The plate-and-hole configuration of the exhaust outlet allows air flow therethrough while capturing larger contamination, such as chipped or broken substrates, from undesirably entering the exhaust system.

Figure 3:
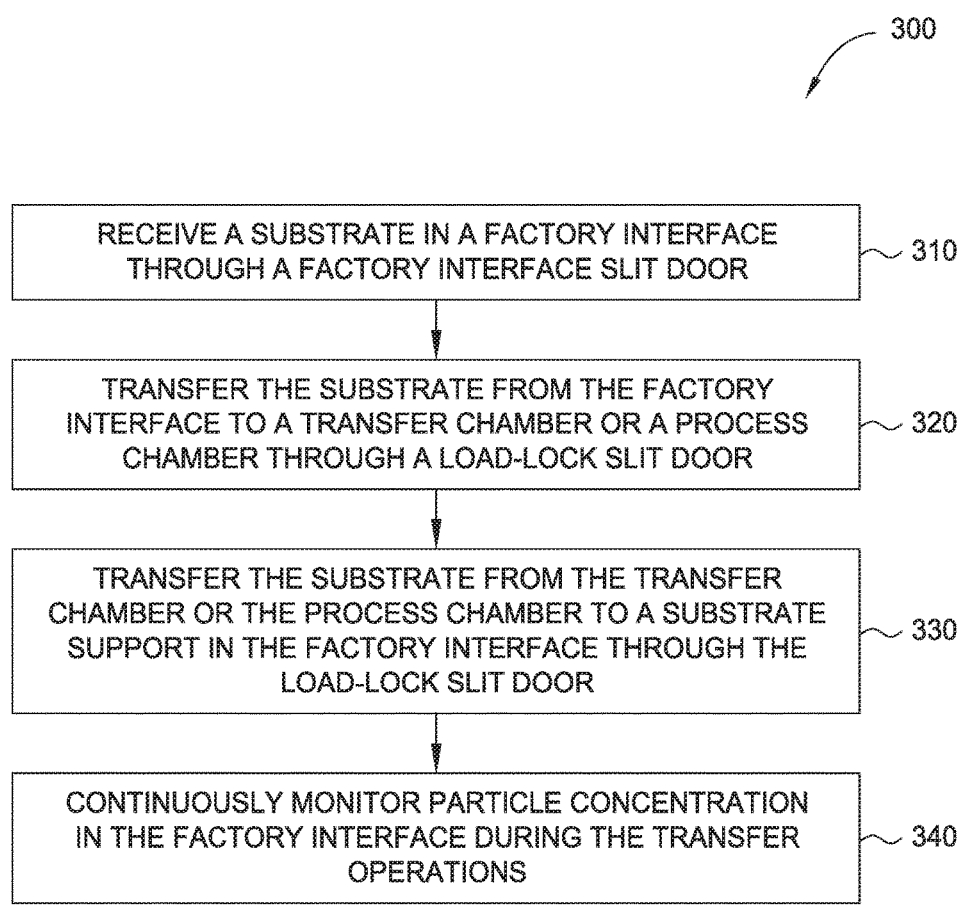
FIG. 3 is a process flow of continuous, in-situ particle detection in an FI of a semiconductor manufacturing system, according to an aspect of the disclosure.

FIG. 3 is a process flow 300 of continuous, in-situ particle detection in an FI of a semiconductor manufacturing system, such as processing system 100. The process flow 300 begins by receiving a substrate in an FI through an FI slit door at operation 310. At operation 320, the substrate is transferred from the FI to a transfer chamber or a process chamber in the semiconductor manufacturing system through a load-lock slit door. Next, the substrate is transferred from the transfer chamber or the process chamber to a substrate support in the FI through the load-lock slit door at operation 330. More particularly, the substrate is transferred back into the FI from the transfer chamber or process chamber for post-processing cool down of the substrate. Oftentimes the substrate spends the longest period of time on the substrate support in the FI for the post-processing cool down. As shown at operation 340, particle concentration in the FI is continuously monitored during the substrate transfer operations. Continuous particle monitoring allows detection of particles that exist or enter from opening the slit valve door, or that are carried in on the robot when grabbing the substrate. Thus, in addition to monitoring particles blown off the substrate by the fan during cool down, the present disclosure provides systems and methods for monitoring particles at other times which occur in the absence of a substrate being present.

In operation, continuously monitoring the particle concentration in the FI begins by directing air via the fan 210 towards the exhaust outlet 290 to create a laminar flow. As shown in the vertical configuration of FIG. 2, the fan 210 directs air downwards over the substrate support 230 and particle detector 260 towards the exhaust outlet 290. In other configurations, the fan 210 may direct air in a horizontal direction over the substrate support 230 and the particle detector 260. The environmental air (e.g., air received the ambient environment within the fabrication facility) is first directed through the filter 220 to remove any particles from the air stream prior to entry into the FI below the filter 220. When the substrate is positioned on the substrate support 230, particles on the surface of the substrate will be entrained in the air stream and off the substrate surface. The air stream and entrained particles are then directed over the particle detector 260 as the air stream is directed towards the exhaust outlet 290. The air stream is received by the tube 270 and analyzed by the particle detector 260.

Figure 4:
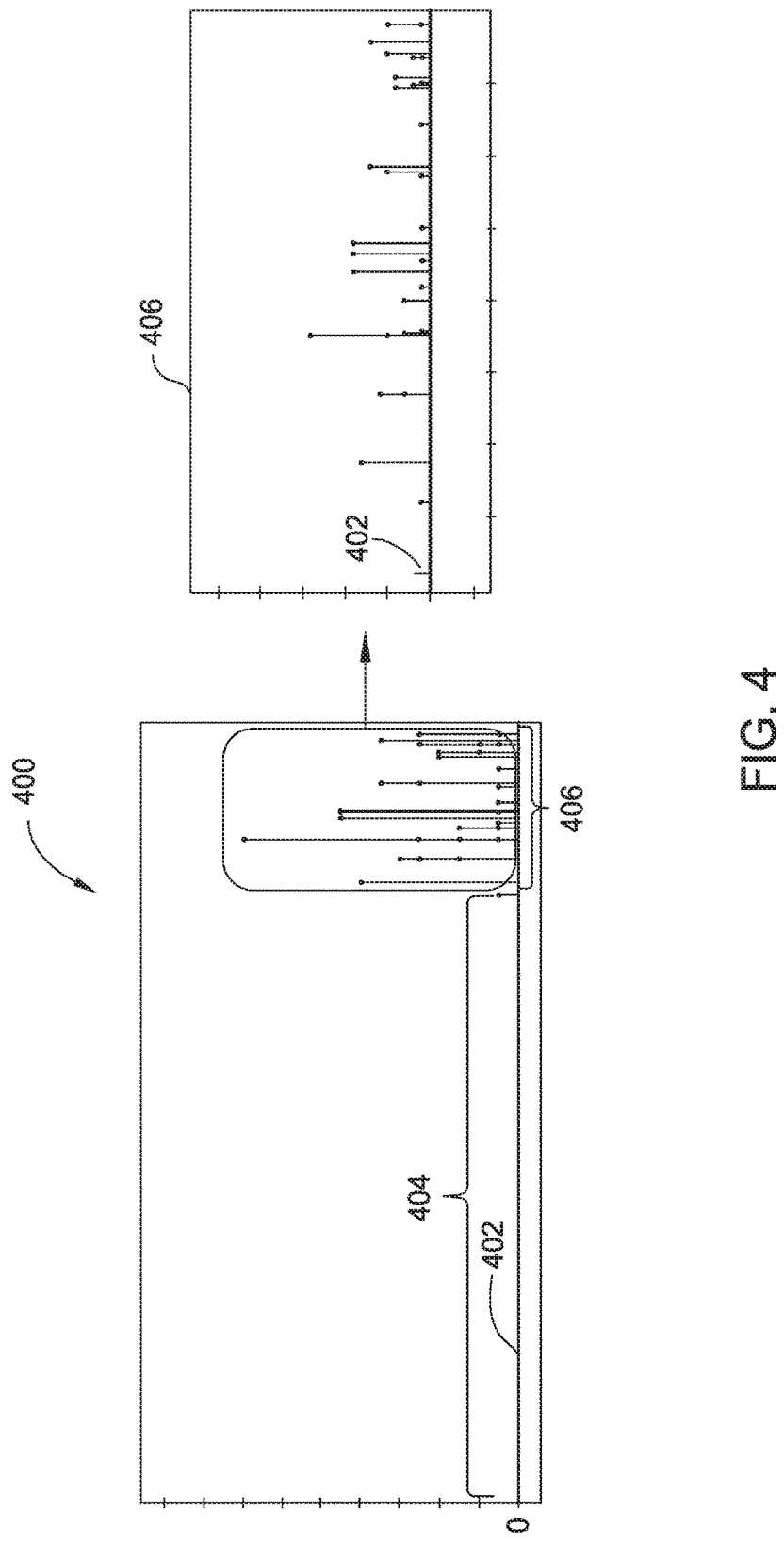
FIG. 4 is a graph of particle concentration detected by a particle detector in an FI over time.

FIG. 4 is a slide showing a graph 400 of particle concentration detected by a particle detector in an FI over time. The y axis corresponds to particle count or concentration and the x axis corresponds to time, such that the graph 400 shows particle concentration in the FI over a period of time. Data line 402 shows the particle concentration detected by a particle detector such as the particle detector 260 of FIG. 2. Over a first time period 404, the data line 402 is linear and shows little to no particle concentration in the FI 203. In other words, the data line 402 over the first time period 404 shows that the FI 203 is running with little to no particle contamination. Over a second time period 406, the particle concentration increases as shown by the peaks of data line 402. The particle concentration in the FI 203 may be the result of numerous events, including but not limited to, reduced fan speed, a pressure difference, an opening of the FI door, or a defective seal.

The data collected by the particle detector 260, such as the data shown in FIG. 4, can be delivered to a system monitoring server and combined with other data collected by other sensors in the factory interface, such as fan speed and pressure sensors, to identify the source of the particle contamination. For example, if the data from the particle detector 260 shows that particle concentration increased over a period of time, the server compares that data with data collected from a sensor, such as a fan speed sensor, to see if the fan speed was reduced over the same period of time and caused the increased particle contamination. The combined data can then be used to quickly identify the root cause of the particle contamination and shorten the time to efficiently troubleshoot the semiconductor processing system.

Figure 5:
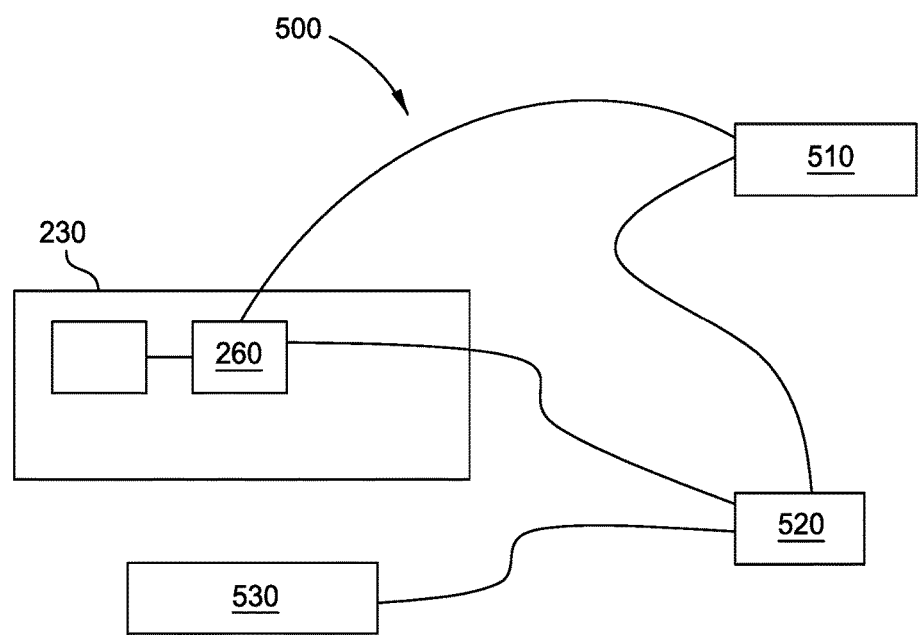
FIG. 5 is a particle detection system, according to an aspect of the disclosure.

In addition, the continuously collected particle detection data may be integrated into a particle detection system 500, as shown in FIG. 5, and used to provide particle contamination alerts to equipment operators. The particle detection system 500 includes the particle detector 260 in the FI 203, which is connected to a power source 510 and a server 520. The server 520 is generally connected to a network 530 for communication, for example, to equipment operators. Other FI detectors may also be connected to the particle detection system 500 to help enable quick troubleshooting when the particle concentration is too high inside the FI 203. For example, in one aspect, one or more additional detectors can be positioned in the FI 203 and connected to the particle detection system 500. In another aspect, one or more additional detectors can be positioned in a second FI and connected to the particle detection system 500. Additionally, in further aspects, the particle detection system 500 is configured to send warning messages through the network 530 when the particle concentration in the FI 203 exceeds a predetermined threshold value. The warning message may indicate the severity of the particle contamination or underlying issue. It is contemplated that different warnings and/or warning messages may be utilized depending on particle contamination severity.

Benefits of the described systems and methods for continuous, in-situ particle detection include, but are not limited to, reduced or eliminated system downtime during particle detection and increased troubleshooting efficiency due to the data collected by the particle detector being combined with other sensor data to identify the source of particle contamination to the FI. In addition, the systems and methods described herein result in increased process yield and decreased substrate scrap rate.

While the foregoing contemplates positioning a particle detector within the FI, the particle detector may also be incorporated into other system components, including but not limited to, a load-lock or buffer chamber.

While the foregoing is directed to aspects of the present disclosure, other and further aspects of the disclosure may be devised without departing from the basic scope thereof, and the scope thereof is determined by the claims that follow.

The invention claimed is:
1. A factory interface, comprising:
a fan for directing air in an airflow direction;
a substrate support positioned downstream from the fan in the airflow direction;

a particle detector coupled to an inner surface of the factory interface and positioned downstream from the substrate support in the airflow direction;

a particle detector tube coupled to the particle detector and open to a location within the factory interface, the particle detector tube being a straight tube aligned in the airflow direction; and an exhaust outlet positioned downstream from the particle detector in the airflow direction.

2. The factory interface of claim 1, further comprising one or more load-lock slit doors, wherein the particle detector is positioned downstream from the one or more load-lock slit doors.

3. The factory interface of claim 1, further comprising a filter, wherein the filter is positioned between the fan and the substrate support.

4. The factory interface of claim 1, further comprising a first substrate holder and effector robot and a second substrate holder and effector robot.

5. The factory interface of claim 4, wherein the particle detector is positioned proximate to and between the first substrate holder and effector robot and the second substrate holder and effector robot.

6. The factory interface of claim 1, wherein the exhaust outlet comprises a baffle plate and a gas outlet.

7. The factory interface of claim 1, further comprising a plurality of particle detector tubes, wherein each of the plurality of particle detector tubes is open to a different location within the factory interface for particle detection of the respective different location.

8. The factory interface of claim 1, wherein the particle detector tube includes an opening along an axial length thereof.

9. The factory interface of claim 8, wherein the opening is at an end of the particle detector tube.

10. The factory interface of claim 9, wherein the opening is disposed at a position below the substrate support.

11. The factory interface of claim 9, further comprising one or more load-lock doors, wherein the opening is disposed at a position adjacent to the one or more load-lock doors.

12. The factory interface of claim 9, further comprising a factory interface door through one or more walls of the factory interface, wherein the opening is disposed at a position adjacent to the factory interface door.

13. The factory interface of claim 1, wherein the particle detector is configured to detect a particle concentration of the air between the fan and the exhaust outlet.

14. The factory interface of claim 1, further comprising:

a server connected to the particle detector, the server being connected to one or more sensors positioned in the factory interface and being configured to collect particle concentration data from the particle detector and the one or more sensors in the factory interface; and a network coupled to the server, the network being configured to communicate particle concentration data and data from the one or more sensors to one or more equipment operators.

15. The factory interface of claim 14, further comprising a second particle detector positioned downstream from a second substrate support in a second factory interface, the server being connected to the second particle detector.

16. The factory interface of claim 14, further comprising a plurality of particle detector tubes, wherein each of the plurality of particle detector tubes is open to a different location within the factory interface for particle detection of the respective different location.

17. A factory interface, comprising:

a fan for directing air in an airflow direction;

a substrate support positioned downstream from the fan in the airflow direction;

a particle detector coupled to an inner surface of the factory interface and positioned downstream from the substrate support in the airflow direction;

a particle detector tube coupled to the particle detector and open to a location within the factory interface, the particle detector tube being a straight tube aligned in the airflow direction, the particle detector tube extending upward from an upper surface of the particle detector and towards the fan; and an exhaust outlet positioned downstream from the particle detector in the airflow direction.

18. The factory interface of claim 17, wherein the particle detector is disposed at a distance from the substrate support, the distance being from about 1 inch to about 24 inches.

19. The factory interface of claim 17, wherein the particle detector tube includes one or more bends.

* * * * *